United States Patent
Kanakaris et al.

(10) Patent No.: US 6,589,990 B1
(45) Date of Patent: Jul. 8, 2003

(54) METHODS AND COMPOSITIONS FOR MISOPROSTOL COMPOUND TREATMENT OF ERECTILE DYSFUNCTION

(76) Inventors: Panagiotis Kanakaris, 33 Koletti Street, GR-106, 77 Athens (GR); Petros Karouzakis, 9 Bakou Street, GR-115, 24 Athens (GR)

( * ) Notice: Subject to any disclaimer, the term of this patent is extended or adjusted under 35 U.S.C. 154(b) by 0 days.

(21) Appl. No.: 09/496,710

(22) Filed: Feb. 2, 2000

Related U.S. Application Data

(63) Continuation-in-part of application No. 09/423,130, filed as application No. PCT/GR98/00012 on Apr. 22, 1998, now Pat. No. 6,210,343.

(30) Foreign Application Priority Data

May 6, 1997 (GR) .................................. 970100
Apr. 22, 1998 (WO) .................. PCT/GR98/00012

(51) Int. Cl.[7] ............... A61K 31/19; A61K 31/557; A61K 31/215; A61K 31/715
(52) U.S. Cl. .................. 514/573; 514/530; 514/58; 514/922; 514/929; 514/946; 514/947
(58) Field of Search ................. 514/573, 530, 514/58, 922, 929, 946, 947

(56) References Cited

U.S. PATENT DOCUMENTS

| | | | |
|---|---|---|---|
| 4,696,821 A | 9/1987 | Belsole | 424/448 |
| 5,242,391 A | 9/1993 | Place et al. | 604/60 |
| 5,252,602 A * | 10/1993 | Alam et al. | 514/530 |
| 5,256,652 A | 10/1993 | El-Rashidy | 514/58 |
| 5,324,746 A | 6/1994 | McKee et al. | 514/530 |
| 5,474,535 A * | 12/1995 | Place et al. | 604/60 |
| 5,510,384 A | 4/1996 | McKee et al. | 514/530 |
| 5,612,359 A | 3/1997 | Murugesan | 514/365 |
| 5,684,177 A | 11/1997 | Lu et al. | 560/121 |
| 5,688,499 A | 11/1997 | Banting et al. | 424/8.35 |
| 5,708,031 A | 1/1998 | Scott | 514/573 |
| 5,773,457 A * | 6/1998 | Nahoum | 514/397 |
| 5,908,853 A * | 6/1999 | Nahoum | 514/341 |
| 5,942,545 A | 8/1999 | Samour et al. | 514/573 |
| 5,962,528 A | 10/1999 | Scott | 514/573 |
| 5,976,566 A | 11/1999 | Samour et al. | 424/449 |
| 5,981,563 A | 11/1999 | Lowrey | 514/400 |
| 6,007,836 A | 12/1999 | Denzer | 424/449 |
| 6,046,244 A | 4/2000 | Buyuktimkin et al. | 514/785 |
| 6,210,343 B1 | 4/2001 | Kanakaris et al. | 600/504 |
| 6,277,884 B1 | 8/2001 | de Tejada | 514/565 |
| 6,294,550 B1 | 9/2001 | Place et al. | 514/302 |
| 6,299,900 B1 | 10/2001 | Reed et al. | 424/449 |
| 6,323,241 B1 | 11/2001 | Yeager et al. | 514/573 |

FOREIGN PATENT DOCUMENTS

| | | | |
|---|---|---|---|
| CN | 1126587 | 1/1995 | A61K/9/06 |
| EP | 1 108 426 | 6/2001 | A61K/31/00 |

(List continued on next page.)

OTHER PUBLICATIONS

Claes, H. et al, *Transcutaneous nitroglycerin therapy in treatment of impotence*, Urol Int., 1989, 44(5):309–12.

Method of Minimum Stereochemical Difference, *Planning of Drugs*, Koyroynakis, P. et al, ed. Graphical Arts, Thessaloniki, p. 159, 1992.

(List continued on next page.)

*Primary Examiner*—Raymond Henley, III
*Assistant Examiner*—Donna Jague
(74) *Attorney, Agent, or Firm*—Bromberg & Sunstein LLP

(57) ABSTRACT

Therapeutic formulations and methods for treating erectile dysfunction with a misoprostol compound in a subject are provided, a method comprising: obtaining a therapeutic formulation having an effective dose of a misoprostol compound in an excipient carrier; and applying the therapeutic formulation topically to the subject.

22 Claims, 1 Drawing Sheet

FOREIGN PATENT DOCUMENTS

| | | | | |
|---|---|---|---|---|
| FR | 2710649 A | 4/1995 | ............ | A61K/7/00 |
| WO | WOPCT91/16021 | * 10/1991 | ............ | A61K/5/41 |
| WO | WO 91/16021 | 10/1991 | ............. | A61F/5/41 |
| WO | WO 93/00894 | 1/1993 | ......... | A61K/31/195 |
| WO | WO 96/03991 | 2/1996 | ......... | A61K/31/557 |
| WO | WO 96/28142 | 9/1996 | ............ | A61K/9/00 |
| WO | WO 97/33608 | 9/1997 | ......... | A61K/38/22 |
| WO | WO 98/50039 | 11/1998 | ......... | A61K/31/557 |
| WO | WO 00/32195 | 6/2000 | ......... | A61K/31/475 |
| WO | WO 01/70211 | 9/2001 | .......... | A61K/31/00 |
| WO | WO 01/70337 | 9/2001 | ............ | A61P/15/00 |
| WO | WO 01/70708 | 9/2001 | ......... | C07D/241/02 |
| WO | WO 02/09717 A1 | 7/2002 | | |

OTHER PUBLICATIONS

The Merck Index, ed. Merck & Co., Inc., 11$^{TH}$ edition, *Misoprostol*, p. 6128, 1989.

Physicians' Desk Reference, ed. Medical Economics Data Production Company at Montreal, 48$^{TH}$ Edition, Arky, MD, R. et al, pp. 2197–2199, 1994.

International Journal of Impotence Research, pp. 9–10, Sep., Montorsi, F. et al, pp. 13–16, 1995.

Goodman & Gilman's The Pharmacological Basis of Therapeutics, Ninth Edition, McGraw–Hill, New York, 1996, p. 8.

Collins, P.W. et al, *Synthesis and Gasric Antisecretory Properties of 15–Deoxy–16–hydroxyprostaglandin E. Analogues*, Journal of Medicinal Chemistry, pp. 1152–1159, 1997.

Campbell's Urology, W.B. Saunders Company, Sixth Edition, vol. III, Goldstein, I. et al, pp. 3053–3057, 1993.

Porst Hartmut, ed. Enke, *Erektile Impotenz*, pp. 68–77, 1992, pp. 88–110.

Tulsi "Delivering the Goods: Drug Delivery Stocks Look Attractive," New Wave Stocks, Intellectual Capital for the Technology Investor, 1997, pp. 1–5.

* cited by examiner

METHODS AND COMPOSITIONS FOR MISOPROSTOL COMPOUND TREATMENT OF ERECTILE DYSFUNCTION

RELATED APPLICATIONS

This application is a continuation-in-part of U.S. application Ser. No. 09/423,130, filed on Nov. 5, 1999 now U.S. Pat. No. 6,210,343 with the United States Patent and Trademark Office, which is a 371 of application PCT/GR98/00012, filed with the Patent Cooperation Treaty on Apr. 22, 1998 and as amended on Jul. 28, 1998; which take priority from application 970100172, filed in Greece on May 6, 1997, and all of which are hereby incorporated by reference herein.

TECHNICAL FIELD

The invention relates to the use of misoprostol, as well as its metabolites, misoprostol acid, for methods and compositions for topical use for the purpose of treating erectile dysfunction (ED).

BACKGROUND

A current pharmaceutical treatment for ED comprises oral administration of sildenafil (Viagra®), a treatment counter indicated for subjects who are: allergic to this material; or are concurrently being treated with a nitrate medicine such as nitroglycerin; a transdermal nitrate; isosorbide nitrate (Imdur®); cimetidine (Tagamet®); mibefradil (Posicor®); or an anti-infective such as erythromycin, ketoconazole, itraconazole, or rifampin. Subjects suffering with ED due to hormonal insufficiency can be treated with suitable steroid hormone substitution therapy. Other current non-oral and non-steroid treatments include mainly the use of intracavernous injections consisting of direct injection of vasodilatory drugs (for example, injections Caverject®; and papaverine, phentolamine) into the corpora cavernosa of the penis (Campell's *Urology*, ed. W.B. Saunders Company, 6th Edition, Volume III, 3055–3057).

Although in situ injection is efficient and scientifically approved, it has serious disadvantages of form (injection) as well as route of administration (introcarvernosal). Yohimbin, an indole alkaloid which is an $a_2$-adrenergic inhibitor, is administrated per os, however the efficiency of this method is questionable (Campell's *Urology*, ed. W. B. Saunders Company, 6th Edition, Volume III, 3053). Nitroglycerin paste has been proposed as a topical composition (Claes, H. et al., 1989 Urol. Int. 44(5): 309–312), however the method has not been developed as a therapeutic because of concerns regarding efficacy and potential serious side effects (Campell's *Urology*, 25th ed. W. B. Saunders Company, 6th Edition, Volume III, 3053). The topical application of prostaglandin $E_1$ (or alprostadil) in the form of an endourethral gel or a stick was recently proposed as a therapeutic to treat male impotence of vascular etiology (*International Journal of Impotence Research*, Stockton ed. Vol. 7, September 1995, Supplement I, 5–6 however it is considered to be of limited efficacy.

A vasodilatory drug or combination of drugs with sufficient transcutaneous absorption, or use of methods (e.g. ionophoresis) which can reinforce the penetration of such drugs through the skin of the mucosal membranes, into the corpora cavernosa of the penis, would be of interest as a potential therapeutic (Campbell's *Urology*, ed. W.B. Saunders company 6th ed., Vol. III, 3057).

Up to the present, the methods intended for external application share the disadvantages of low efficiency, high cost, potential serious side effects, and discomfort of routine injection. The greatest technical difficulty that must be overcome for development of a method of topical use to reverse ED, is penetration of drugs through various barriers of skin and mucosa to reach the corpora cavernosa, in sufficient concentration to be effective in producing an erection.

SUMMARY

An embodiment of the invention provides a method for treating erectile dysfunction in a subject, comprising: (a) obtaining a therapeutic formulation having an effective dose of a misoprostol compound in an excipient carrier; and (b) applying the therapeutic formulation topically to the subject, for example, to the glans penis, the mucosa, or other area of skin. According to an embodiment of this method, the misoprostol compound comprises one or more of the group of: a purified stereoisomer, a racemic mixture, a mixture of purified stereoisomers, and a racemic mixture and a purified stereoisomer. Further, the stereoisomer is selected from the group of an R form and an S form, and a (+) and a (−) enantiomer is selected from an R form and an S form. The misoprostol compound comprises a racemic mixture of (+) and (−) enantiomers of R and S stereoisomers, for example, the racemic mixture of (+) and a (−) enantiomers of R and S stereoisomers are present in substantially equal proportions. Further the stereoisomer is selected from the group of (±)-R forms and (±)-S forms at the carbon atom at position 16 of the misoprostol compound.

According to an embodiment of this method, obtaining the therapeutic formulation in (a) includes selecting a topical delivery format from the group of: a solution, an ointment, a gel, a stick, and a transdermal patch. According to a further embodiment of this method, (b) includes applying an effective dose which is substantially equivalent to about 0.05 to 0.25 ml of a 0.9 percent formulation by weight of the misoprostol compound. In an alternative embodiment, (b) includes applying an effective dose which is substantially equivalent to at least 0.25 ml of a 0.9 percent formulation by weight of the misoprostol compound.

In a further embodiment of the invention, step (a) comprises adding an agent having synergistic activity in combination with the misoprostol compound, for example, the agent having synergistic activity is a vasodilatory substance, for example, the vasodilatory substance is alprostadil. The misoprostol compound may act as a penetration enhancer for the agent. In an alternative embodiment of the method, the agent having synergistic activity in combination with the misoprostol compound is a penetration enhancer. The agent in combination with the misoprostol compound has a synergistic effect that is selected from the group of: reducing the effective dose, prolonging the therapeutic result, and reducing or eliminating a side effect of the therapeutic formulation. For example, agent is α-cyclodextrin, and the α-cyplodextrin reduces or eliminates a side effect of the therapeutic formulation having a dose of greater than about 2000 micrograms of the misoprostol compound.

In another embodiment of the method, formulation further comprises one or more compounds selected from the group of: α-cyclodextrin, propylene glycol, hydroxypropyl methylcellulose, and glycerol. According to this embodiment, the α-cyclodextrin is present in an amount of 0% to about 1.6%, the propylene glycol is present in an amount of 0% to about 10%, the hydroxypropyl, methylcellulose is present in an amount of 0% to about 2.5%, and glycerol is present in an amount of 0% to about 7.0%.

Another embodiment of the method comprises in step (b) further determining a dosage unit which is an effective dose for the subject, the dosage unit being an amount of the therapeutic formulation applied to the glans penis for an effective period of time to achieve an erection.

Another embodiment of the method comprises in step (b) further determining a dosage unit which is an effective dose for diagnosis of vascular damage in the subject, the dosage unit being an amount of the therapeutic formulation applied to the glans penis sufficient to further perform: (c) determining vascular damage by the Doppler method or cavernosometry.

An embodiment of the invention provides an erectile dysfunction therapeutic composition, comprising an effective dose of a misoprostol compound in a topical formulation. The topical formulation is selected from the group of: a solution, an ointment, a gel, a stick, and a transdermal patch. In this embodiment, the misoprostol compound comprises one or more selected from the group of: a purified stereoisomer, a racemic mixture, a mixture of purified stereoisomers, and a mixture of a racemic mixture and a purified stereoisomer. An example of this embodiment is a composition further comprising an agent having synergistic activity in combination with the misoprostol compound, for example, a composition wherein the agent having synergistic activity is a vasodilatory substance, for example, the vasodilatory substance is alprostadil.

In another embodiment, the composition comprises further a penetration enhancer. In yet another embodiment, the composition comprises further α-cyclodextrin.

DETAILED DESCRIPTION OF SPECIFIC EMBODIMENTS

The present compositions and methods aim at eliminating the disadvantages of prior methods and compositions to treat male impotence.

Figure 1:
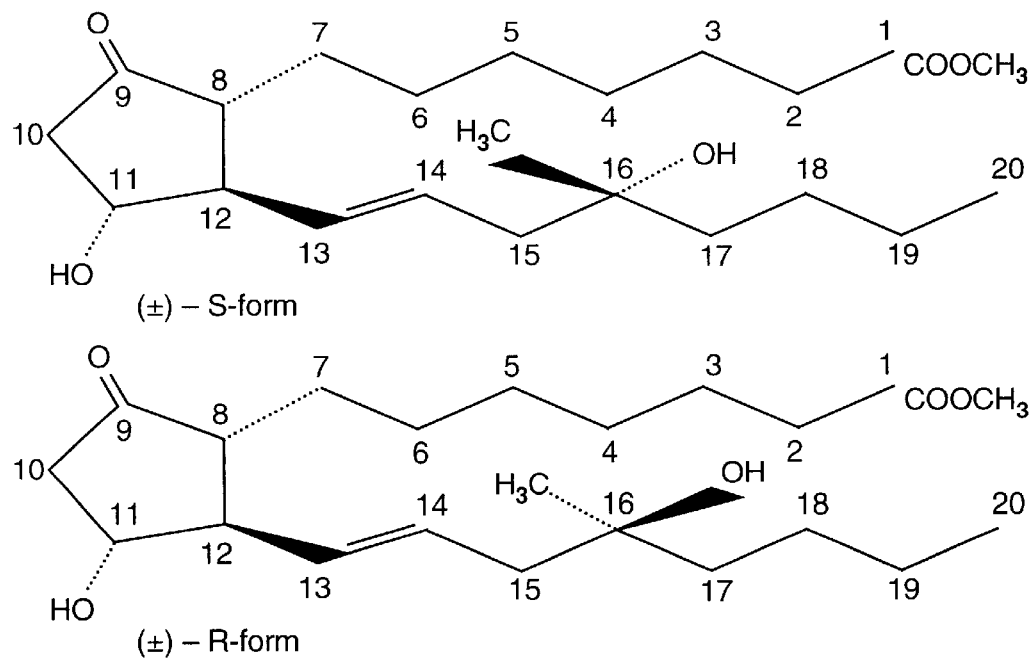
FIG. 1 shows the (±)-S forms and -R forms of misoprostol.

Misoprostol is the general name of a synthetic prostaglandin belonging to the $E_1$ series ($PGE_1$ analogs). Synthesis of misoprostol is described by: P. W. Collins, et al., Belgian Patent 827,127; and U.S. Pat. No. 3,965,143; see also The Merck Index, ed. Merck & Co., Inc., 11th edition, 1989, 6128. The chemical name for misoprostol is (11a 13E)-(±)-11,16-dihydroxy-16-methyl-9-oxoprost-13-en-1-oic acid methyl ester, or (±)-(methyl)-(1R,2R,3R)-3-hydroxy-2-[(E)-(4RS)-4-hydroxy-4-methyl-1-octenyl]-5-oxocyclopentaneheptanoate, or (±)-15-deoxy-(16RS)-16-hydroxy-16-methyl-$PGE_1$ methyl ester. The empirical formula is $C_{22}H_{38}O_5$. The structural formula is shown in FIG. 1. Four steroisomers can be found in about equal proportions (the (+) and (−) enantiomers of the 16-R- and 16-S-forms; Merck Index, 11th edition, 1989, 6128). In contrast to other prostaglandins of group $E_1$ and especially alprostadil, misoprostol bears a methyl group (—$CH_3$) on the carbon atom at position 16. According to a method which can relate biological action of a medicament molecule to its chemical structure (method of minimum sterochemical difference, in "Planning of Drugs," P. Kourounakis, E. Rekka, ed., Graphical Arts, Thessaloniki, 1992, p. 152), the presence of the methyl group provides for substantial penetration of misoprostol into underlying tissues, producing local vasodilation which can treat the ED condition.

A "misoprostol compound", as used here and in the claims, means misoprostol and any of its metabolites, derivatives, analogs, precursors, and enantiomeric forms. A misoprostol compound comprises inorganic and organic salts, and organic and inorganic esters of misoprostol, misoprostol acid, and other metabolites, derivatives, analogs, precursors and enantiomorphic forms of misoprostol and misoprostol acid.

Unless the context otherwise requires, the terms and phrases defined below as well as throughout this description, shall be understood to have the meanings set forth, for purposes of both this description and the following claims.

The term "erectile dysfunction" (ED) means the absence or insufficiency of obtaining a penile erection, with respect to hardness and duration of maintenance.

The term "topical" refers to administration of a therapeutic substance by application to skin or mucosa of the penis.

The term "skin" refers to the epidermal layer of the epithelium of the penis, including the prepuce, and includes the stratum corneum and basal cell layers.

The term "effective dose" means that amount of a therapeutic agent sufficient to cause and erection to form within the time period of 20–40 min from initial application. The doses which are mentioned in the examples herein specifically suggest of a range of potential doses, since the intensity of the result depends, apart from the cause and the grade of the ED or other factors, e.g. the degree of moisture of the underlying tissue, for example variation due to circumcision, the physiological condition of the skin or the mucosa, etc. As the overall effect of these factors can vary among individuals, a suggested range of doses would involve initially using a lower dose, and repeating that dose until a satisfactory erection is obtained within the time period. A moisturizing agent or penetration enhancer can be added to a formulation of an administered dose.

Misoprostol is currently used as an oral antiulcer drug (Physicians Desk Reference, PDR, ed. Medical Economics Data Production Company, Montvale, N.J., 48th edition, 1994, 2197–2199), specifically, misoprostol is administered for prevention of gastric ulcer in patients concurrently taking non-steroidal anti-inflammatory drugs. It is available in European countries and in the U.S. from Searle Company under the commercial name Cytotec®. In no country is the drug mentioned as suitable for treatment of male impotence, nor has such a use been reported in the international scientific literature or patents. On the contrary, among the undesirable effects of oral therapy with misoprostol is male impotence (Physicians Desk Reference, ed. Medical Economics Data Production Company, Montvale, N.J., 48th edition, 1994, p. 2197–2199). Therefore, the embodiments of the present invention for topical use for reversing ED are surprising, in view of previous use and documented side effects of oral administration of misoprostol, and in view of lack of efficacy of alprostadil.

Misoprostol is less active in causing vasodilatory action compared to alprostadil, when each is provided into the corpus cavernosum. However, misoprostol causes greater vasodilation compared to alprostadil when each is applied topically. This is due to the differences in the mechanism of action on erectile function between misoprostol and other vasodilators (e.g. alprostadil): misoprostol applied topically can penetrate into the corpora cavernosa and can act on the smooth muscle fibers of the vessels, compared to other vasodilators. Further, its major site of action is on the vessels of the glans penis, and to a lesser extent, the prepuce.

Because of strong vasodilation caused by topical use of misoprostol, topical application causes significant flow of blood into these vessels. Consequently, a natural negative pressure in the corpora cavernosa is created, which is balanced by the entrance of abundant blood into these bodies, resulting in induction of an erection. In other words, the glans vessels act as "blood pumps," and by that mechanism, the erectile function is rapidly effected.

In an embodiment of the invention, the nature and extent of response to smaller doses of misoprostol (as measured by durability and hardness of erection) depends on the physiological condition and correct functioning of the penile vasculature. Therefore, misoprostol can be used as an accessory diagnostic means (instead of papaverine or alprostadil) in the Doppler method or in cavernosometry, to determine the capacity of the blood vessel system, for determining the extent and nature of vascular damage. (For use of a vasodilatory drug as an accessory diagnostic means in the "Doppler" method or cavernosometry, see *Erektile Impotenz*," ed. Enke, p. 68–77 and p. 88–110.)

Figure 2:
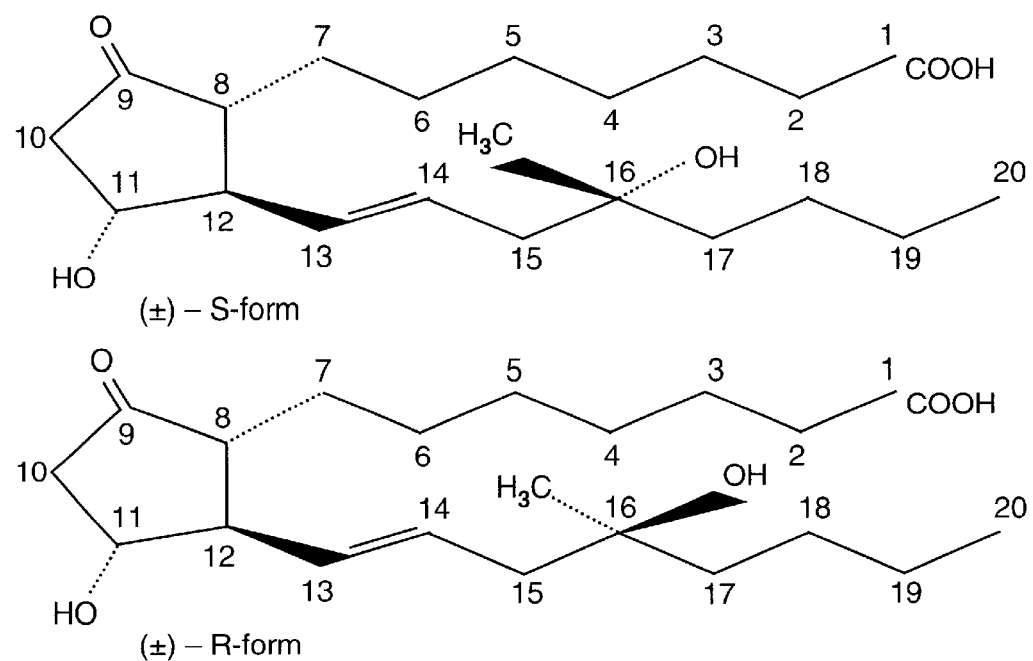
FIG. 2 shows the (±)-S forms and -R forms of misoprostol acid, which is a metabolite of misoprostol.

The hydrolysis product of misoprostol, misoprostol acid, which is the first misoprostol metabolite to appear in vivo after administration of misoprostol to an organism, exerts equivalent strong topical vasodilation upon external application. The structure of misoprostol acid is shown in FIG. 2.

Because of the topical vasodilatory action of each of misoprostol and misoprostol acid, these molecules can facilitate absorption and penetration of other drugs through the skin and other layers such as the mucosa. In other words, these molecules act as "penetration enhancers," to facilitate absorption of other potentially synergistic agents (e.g. alprostadil) through the skin and the mucosa, resulting in high concentrations of the drugs entering underlying tissues, and especially the corpora cavernosa. Thus the facilitated drugs can act in concert with the compositions comprising misoprostol and misoprostol acid, which are embodiments of the present invention, and can exert a synergistic action. Misoprostol is water soluble, and its compatibility with a variety of excipients provides the opportunity for production of a variety of pharmaceutical formulations for topical use, which can be well tolerated by the skin and the mucosa. The fact that misoprostol is extremely hydrophilic compared with other prostaglandins of the $E_1$ series confers a number of advantages to the methods and compositions embodied herein. For example, alprostadil can be dissolved in alcohol, but solubility in water is only 8000 micrograms/100 ml at 35° C.). Thus with alprostadil and other molecules, the presence of one or more organic chemicals is required (e.g. ethyl alcohol), which can irritate tissues and are thus unsuitable for application on the skin and especially the mucosa. Further, as incorporation of the active substances of the embodiments of the present invention in a very small volume of excipient is enabled, the compositions are suitable for application to surfaces of limited area, e.g. the urethra or the glans penis.

Example 1 shows two different formulations of gels of low viscosity having a misoprostol compound, and describes a range of effective doses. Example 2 shows two different formulations of gels of moderately high viscosity having a misoprostol compound for endourethral application, and describes a range of effective doses. Example 3 shows formulations of solutions having a misoprostol compound, and describes a range of effective doses and possible additives to increase the viscosity of the formulation.

Example 4 shows a formulation of a misoprostol compound which has a vanishing cream base, for use as an ointment or an emulsion, and describes a range of effective doses. Example 5 shows a formulation of a misoprostol compound as a stick for endourethral insertion. Example 6 shows a formulation having a misoprostol compound and α-cyclodextrin.

Example 7 shows a formulation of a misoprostol compound having also alprostadil and ethyl alcohol. Example 8 describes effects, if any, of variables such as pH, temperature of formulation, and various additional components on the activity of a misoprostol compound. Example 9 describes use of a single dose high amount of a misoprostol compound. Example 10 describes clinical trials with human male subjects of formulations of the invention in comparison with other compositions, among classes of subjects having ED of different etiologies.

Ranges of effective doses for misoprostol treatment of ED vary depending both on the route of administration and the formulation. Clinical trials in human males used 80–100 µg of gel applied topically or endourethally (Example 10). Dose ranges lower than this range, for example, from 20–40 µg, can be applied topically as a gel, cream, emulsion, or solution. Effectiveness can vary among different subjects because of different etiologies of the condition, and because of extent of moisture of the glans mucosal tissue. Higher doses, for example, 0.1–0.25 mg, 0.2–0.5 mg, 0.4–0.9 mg (Examples 1, 2, 3, 5, 6, and 7) can also be effective topically or endourethally, depending on responses of the subjects. Further, very high dose ranges can be employed when administered as a single dose in a formulation with α-cyclodextrin (Example 9).

The compositions and methods which are the embodiments of the present invention overcome a serious technical obstacle, i.e., the inefficiency with which a potential topical treatment for ED can pass through various barriers of the skin and the mucosa, to reach the corpora cavernosa in sufficient concentration.

The methods and compositions that are the embodiments of the invention herein provide significant advantages, including a route of administration of the drug which is topical, the lack of undesired side effects at the suggested doses of the formulations, low cost, and satisfactory results of the erection that is produced.

EXAMPLES

The examples infra relate to additional embodiments of pharmacological forms and methods of application of a misoprostol compound. The term "misoprostol" as used in the examples and tables includes at least one of a misoprostol compound.

Example 1

Formulation as a Low Viscosity Gel

Among compositions which are embodiments of the invention is a gel of relatively low viscosity, which has: 0.9% w/v of a misoprostol compound, and substances suitable for the formation of a gel, e.g. hydroxypropyl methylcellulose 3000 2% w/v, propylene glycol 10% v/v, and purified water, formulated to a total of 100 ml. The gel thus formulated contains 9 mg of active substance per ml.

The method of application comprises application of about 0.1–0.25 ml of the formulation (or less or more, depending on the response of the individual subject) to the glans penis, the prepuce, or both. More specifically, a volume of about 0.05–0.20 ml of the gel of relatively low viscosity containing 0.9% w/v of a misoprostol compound is applied to the glans penis or to the prepuce.

TABLE 1

Formulations of low viscosity gels of Example 1.

| Formulation 1 | misoprostol | 0.9 g |
| --- | --- | --- |
|  | hydroxypropyl methylcellulose 3000[a] | 2 |
|  | water, purified | to 100 ml |
| Formulation 2 | misoprostol | 0.9 g |
|  | sodium carboxymethylcellulose[b] | 2 g |
|  | propylene glycol | 25 ml |
|  | water, purified | to 100 ml |

[a]available from Dow Corp., Midland MI, or Carbomer, Inc., Westborough, MA
[a]available from F. C., Philadelphia, PA Example 2

Formulation as a High Viscosity Gel for Endourethral Application

A volume of about 0.05–0.20 ml gel of relatively high viscosity, containing 0.50% w/v of a misoprostol compound is provided for endourethral application at a depth 2–5 cm from the outside of the urethral opening.

TABLE 2

High viscosity gel formulations of Example 2.

| Formulation 1 | misoprostol | 0.5 g |
| --- | --- | --- |
|  | hydroxypropyl methylcellulose 3000 | 4 g |
|  | water, purified | to 100 ml |
| Formulation 2 | misoprostol | 0.5 g |
|  | sodium carboxymethylcellulose | 4 g |
|  | propylene glycol | 25 ml |
|  | water, purified | to 100 ml |

Example 3

Formulation as a Solution

A volume of about 0.05–0.20 ml of aqueous solution of a misoprostol compound containing 0.9% w/v is provided for application to the glans penis or the prepuce. The solution can also contain propylene glycol or glycerol in the corresponding proportions (e.g. 10%) to increase the viscosity of the solution.

Example 4

Formulation as an Emulsion and as an Ointment

A volume of about 0.05–0.20 ml of an ointment or emulsion containing 0.9% w/w of a misoprostol compound in a vanishing cream is provided to apply to the glans penis or to the prepuce. The misoprostol compound is formulated in a continuous aqueous phase.

TABLE 3

Formulation of Example 4 in a vanishing cream.

| Formulation | misoprostol | 0.9 g |
| --- | --- | --- |
|  | vanishing cream | 100 g |

The vanishing cream used in this example was Bepanthene® Cream (Roche). Various other vanishing creams and other emollients which are available and familiar to one of ordinary skill in the art of specialty formulations, and are described in National Pharmacopeias, can be used for the formulation of a misoprostol compound as an emulsion or an ointment.

Example 5

Endourethral Sticks

Endourethral sticks of suitable dimensions, weight about 50 mg, containing a misoprostol compound, 0.04–0.20% w/w are provided to insert into the urethral mucosa.

An endourethral stick can, in various embodiments of the invention, provide from 10 to 60 mg of a misoprostol compound, for example, 10–30 mg, 20–40 mg, 30–50 mg, and 40–60 mg.

TABLE 4

Formulation of endourethral sticks of Example 5.

| Formulation | misoprostol | 0.04–0.20 g |
| --- | --- | --- |
|  | glycerol | 70 g |
|  | gelatin | 20 g |
|  | water, purified | to 100 g |

Example 6

A Gel Comprising α-Cyclodextrin

A volume of about 0.05–0.25 ml of gel (or more or less) depending on the response of the subject) is provided according to the Example 1, formulation 1 of Table 1, and Example 2, formulation 1 in Table 2 above, which contains in addition 1.6% w/v α-cyclodextrin (Carbomer, Inc., Westborough, Mass., or Cerestar USA, Hammond, Ind.) formulated as 1.6 g α-cyclodextrin per 100 ml. The optional addition of a complex forming means, such as 1.6% w/v α-cyclodextrin, to the compositions of Examples 1 and 2 can have a significant effect in reduction of side effects of high doses of a misoprostol compound, as described in a further example herein.

Example 7

A Gel Comprising an Additional Drug, Alprostadil, and an Alcohol

A volume of at least 0.05–025 ml gel (depending on response) according to the formulation of Example 6 is provided, which contains in addition 10 ml of ethyl alcohol (96%) and 0.5 mg/ml alprostadil (Pharmacia & Upjohn, Kalamazoo, Ind.) formulated as 50 mg of alprostadil dissolved in the 10 ml of ethyl alcohol, per 100 ml of final gel as in Example 6.

Example 8

Influence of Temperature of Formulation, pH, Addition of Specific compound and Time of Application Formulation of a misoprostol compound in the bases described in the examples herein was performed at room temperature (20–25° C.), not exceeding 40° C. No significant change in misoprostol activity was observed as a function of the pH values of the various bases, however significant reduction or/and neutralization of misoprostol activity was observed in the presence of Polysorbate 80.

A positive result of application of an effective dose of a composition described herein can be observed from about 20–40 minutes after the time of application. Both the rapidity of the appearance of a positive result, and the intensity of the result were enhanced by the presence in the formulation of certain moisturizing agents such as propylene glycol and/or glycerol. Further, compounds capable of enhancing the transcutaneous absorption of a misoprostol compound, such as urea and citric acid, were observed also to reduce the time interval for and enhance the intensity of the result. Urea and citric acid serve both as penetration enhancers and as moisurizing agents. Citric acid can be added at about 0.1%, w/w, and urea can be added at about 0.5%, w/w, for example, citric acid can be added from 0.01–0.05%, 04–0.08%, and 0.06–0.1%. Urea can be added to about 0.05–0.2%, 0.1–0.3%, 0.2–0.4%, and at about 0.3–0.5%.

Example 9

Single High Dosage

A single high dose of a misoprostol compound (>1800 micrograms on the glans penis and >1000 micrograms in the urethra), rather than application of a series of smaller-doses, can cause certain systemic undesirable effects such as fatigue, erythema and diarrhea. The presence of α-cycodextrin reduces or eliminates the undesirable effects, and allows the application of a single higher dose (>2000 micrograms). Such formulation as a single dose can have the advantages of reduction of significant delay in time of action, and can enhance the intensity of the result and extent of its duration.

Example 10

Clinical Trials in Human Male Subjects Having ED

Subjects were 52 men aged 22–67 years, with ED of various causes. In 24 of the subjects it was reported that ED was due to vascular causes, in 5 to neurogenic causes, in 5 due to psychological problems, and in 1 case due to hormonal reasons, while in 7 subjects ED was due to different or unknown causes. In all trials with these subjects, the following methods were applied successively for from a few days to 4 weeks: intracavernosal injection of 1.0 ml papaverine solution, 40 µγ/ml; intracavernosal injection of 0.5 ml alprostadil, 20 µg/ml; intraurethral application of 0.1 ml $PGE_1$ ointment, 1000 µg/ml; topical application to the glans penis 0.08 to 0.1 ml, misoprostol gel 1000 µg/ml; intraurethral application of 0.08 to 0.1 ml misoprostol gel 1000 µg/ml; and topical application to the glans penis 0.1 ml. Gel of placebo.

In the tests using either the gel or cream containing about 1000 µg of misoprostol per 0.1 ml, the formulation was applied by the patients themselves using their finger and a few retroactive movements of the prepuce on the glans of penis until the ointment was completely absorbed. The intraurethral gel was instilled by the patients with help of a thin syringe and a lubricating medium (propylene glycol or glycerin) to facilitate insertion of the syringe. After the applying the formulation containing the misoprostol formulation or other compound or placebo control, it was suggested that the patient remain seated until the appearance of a pharmacological result.

In some patients with venous leak problems, a bandage tourniquet with a rubber band (or condom) on the base of the penis was applied 15–20 minutes after application of misoprostol. This method was particularly effective. On the contrary, preliminary bandaging (before or during application) had a pharmacologically inhibitory effect. In various subjects with ED due to one of several different causes, "pelvic exercises" were recommended (Kegel exercises) while the erection was developing. The results of this method were particularly satisfactory in some subjects, but several other subjects noted that they did not understand the indication and consequently did not comply. All tests were performed in the clinic without visual or any other type of stimulation.

Results of these treatments on the subjects were compared (see Table 5). According to Table 5, results from the application of misoprostol on the glans penis or the urethra were clearly superior, compared with those of intraurethral application of alprostadil and intracavernosal injection or papaverine. These were approximately equal to intracavernosal injection of alprostadil. Compared to results obtained, using other methods, e.g. alprostadil for intraurethral use, the pharmacological results of misoprostol were stronger and had a greater durability, plus significantly lower cost. It is notable that although in all cases the same dose was applied (approx. 800 µg) so that results could be evaluated, several subjects responded satisfactorily to lower doses (100–200 µg).

On another sample of 7 patients with ED due to vascular cause, which had not previously responded to intraurethral application of $PGE_1$ ointment (1000 µg), 3 responded satisfactorily to a combination of $PGE_1$ and misoprostol (1000 and 200 µg, respectively) in the form of an intraurethral gel. Some subjects reported that several hours after leaving the clinic they experienced prolonged tumescence, which developed into an erection sufficient for vaginal penetration. Another group of subjects with psychogenic impotence reported that a low dose of misoprostol (100–200 µg) was sufficient to cause a sub-optimal erection which, after genital and/or audio-visual sexual stimulation, developed into an erection sufficient for sexual intercourse.

The doses mentioned are merely indicative, as absorption of misoprostol depends on several factors, such as the degree of moisturizing of the underlying tissue and the physiological state of the glans penis or the urethra (e.g. with inflammatory diseases the absorption and pharmacological results appear faster and with a greater intensity). No allergic or any other topical reaction was reported except for redness of the glans, which is caused by local vasodilation.

TABLE 5

Pharmacological effects of formulations on ED subjects having varying etiologies.

| etiology (N) | papaverine | $PGE^b$ | $PGE_1{}^c$ | misoprostol[d] | misoprostol[e] | placebo[f] |
|---|---|---|---|---|---|---|
| vascular (N = 24) | 7 | 10 | 5 | 10 | 13 | 0 |
| psychogenic (N = 15) | 10 | 11 | 9 | 13 | 14 | 1 |
| neurogenic (N = 5) | 2 | 4 | 1 | 4 | 5 | 0 |

TABLE 5-continued

Pharmacological effects of formulations on ED subjects having varying etiologies.

| etiology (N) | papaverine | PGE[b] | PGE$_1$[c] | misoprostol[d] | misoprostol[e] | placebo[f] |
|---|---|---|---|---|---|---|
| hormonal (N = 1) | 0 | 1 | 0 | 1 | 1 | 0 |
| undetermined (N = 7) | 3 | 5 | 1 | 4 | 5 | 1 |
| total (N = 52) | 22(42%) | 31(60%) | 16(31%) | 32(62%) | 38(73%) | 2(4%) |

The numbers within the boxes indicate those subjects having a positive pharmacological outcome from treatment by the formulation. N indicates the total number of subjects having ED of a particular etiology.
[a]Papaverine (1 ml of 4%) was administered by intracavernosal injection.
[b]PGE$_1$ 0.5 ml of 1.0 mg/ml was administered by intracavernosal injection.
[c]PGE$_1$ was administered as an ointment (0.1 ml, Macrogol "300" 650 mg, Macrogol "4000" 350 mg), or PGE$_1$ γ-cyclodextrin complex (corresponding to 1000 μg PGE$_1$) in 0.1 ml K-Y ® jelly for intraurethral use.
[d]Misoprostol (80–100 μg) was administered as an externally applied gel.
[e]Misoprostol (80–100 μg) was administered as an intraurethral applied gel.
[f]Placebo (80–100 μg) was administered an as externally applied gel.

What is claimed is:

1. A method for treating erectile dysfunction in a subject needing such treatment, comprising:
    externally to the penis administering a vasoactive formulation having an effective dose of an active agent, wherein the active agent consists of a misoprostol compound, for treating erectile dysfunction in the subject.

2. A method according to claim 1, wherein the misoprostol compound comprises one or more of the group of: a purified stereoisomer, a racemic mixture, a mixture of purified stereoisomers, and a racemic mixture and a purified stereoisomer.

3. A method according to claim 1, wherein the stereoisomer is selected from the group of an R form and an S form.

4. A method according to claim 3, wherein the stereoisomer is selected from the group of (±)-R forms and (±)-S forms at the carbon atom at position 16 of the at least one of misoprostol and misoprostol acid.

5. A method according to claim 1, wherein a (+) and a (−) enantiomer is selected from an R form and an S form.

6. A method according to claim 1, wherein the misoprostol compound comprises a racemic mixture of (+) and (−) enantiomers of R and S stereoisomers.

7. A method according to claim 6, wherein the racemic mixture of (+) and (−) enantiomers of R and S stereoisomers are present in substantially equal proportions.

8. A method according to claim 1, wherein the formulation is in a form selected from a solution, an ointment, a gel and a transdermal patch.

9. A method according to claim 1, wherein the effective dose of the misoprostol compound is about 0.05 to about 0.25 ml of a 0.9 percent formulation by weight.

10. A method according to claim 1, the effective dose is at least 0.25 ml of a 0.9 percent formulation by weight of the misoprostol compound.

11. A method according to claim 1, wherein the effective dose is no more than 800 mcg of the misoprostol compound.

12. A method for treating erectile dysfunction in a subject needing such treatment, comprising:
    topically administering a formulation containing an effective dose of a synergistic mixture of a first agent consisting of a misoprostol compound and a second penile erection stimulating agent other than a histamine, histamine receptor agonist or an alpha blocker for treating erectile dysfunction in the subject.

13. A method according to claim 12, wherein the second agent is alprostadil.

14. A method according to claim 13, wherein the misoprostol compound acts as a penetration enhancer for alprostadil.

15. A method according to claim 12, wherein the second penile erection stimulating agent has at least one beneficial effect selected from: reducing the effective dose, enhancing the treatment, or reducing or eliminating a side effect of the formulation.

16. A method according to claim 15, wherein the second compound is selected from one or more of: α-cyclodextrin, propylene glycol, hydroxypropyl methylcellulose, and glycerol.

17. A method according to claim 12, wherein the second penile erection stimulating agent is α-cyclodextrin.

18. A method according to claim 17, wherein the α-cyclodextrin is present in an amount of 0% to about 1.6%, propylene glycol is present in an amount of 0% to about 10%, the hydroxypropyl methylcellulose is present in an amount of 0% to about 2.5%, and glycerol is present in an amount of 0% to about 70%.

19. A method for treating erectile dysfunction in a subject needing such treatment, comprising:
    topically administering a formulation having an effective dose of an active agent, the active agent consisting essentially of a mixture of a misoprostol compound and alprostadil to a surface of the penis, the surface selected from skin or prepuce of the glans penis for treating erectile dysfunction in the subject.

20. A method of treating erectile dysfunction in a subject needing such treatment, comprising:
    externally administering a vasoactive formulation containing an effective dose of a mixture of a first agent consisting of a misoprostol compound and a second penile erection stimulating agent to the penis of a subject such that the misoprostol compound facilitates penetration of second agent into the penis to stimulate an erection.

21. A method according to claim 20 wherein the second penile erection stimulating agent is alprostadil.

22. A method according to claim 20 wherein the second penile erection stimulating agent is α-cyclodextrin.

* * * * *

UNITED STATES PATENT AND TRADEMARK OFFICE
CERTIFICATE OF CORRECTION

PATENT NO.     : 6,589,990 B1
DATED          : July 8, 2003
INVENTOR(S)    : Panagiotos Kanakaris et al.

It is certified that error appears in the above-identified patent and that said Letters Patent is hereby corrected as shown below:

Column 1,
Line 24, change "counter indicated" to -- counter-indicated --.
Line 42, change "introcarvenosal" to -- intracavernosal --.
Lines 49 and 54, insert -- one -- after "therapeutic".
Line 57, insert -- ; -- after "5-6".
Line 62, delete "," after "membranes".
Line 64, insert -- one -- after "therapeutic".

Column 2,
Line 3, insert -- the -- after "for".
Line 33, change "format" to -- form --.
Line 65, delete "," after "hydroxypropyl".

Column 3,
Line 50, insert -- , -- after "(11a"
Line 57, change "steroisomers" to -- stereoisomers --.

Column 4,
Line 24, change "and" to -- an --.
Line 27, delete "of" after "suggest".
Line 29, change "or" to -- on --.
Line 30, delete "for example" after "after".

Column 6,
Line 19, change "gel" to -- misoprostol --.
Line 19, change "endourethally" to -- endourethrally as a gel --.
Line 64, change "0.1-0.25" to -- 0.01-0.25 --.

Column 7,
Line 43, change "containing 0.9% w/v" to -- containing 0.9% w/v misoprostol --.
Line 46, change "10%" to -- 10% v/v --.

UNITED STATES PATENT AND TRADEMARK OFFICE
CERTIFICATE OF CORRECTION

PATENT NO. : 6,589,990 B1
DATED : July 8, 2003
INVENTOR(S) : Panagiotos Kanakaris et al.

It is certified that error appears in the above-identified patent and that said Letters Patent is hereby corrected as shown below:

Column 8,
Line 46, change "0.05-025 ml" to -- 0.05-0.25 ml --.
Line 61, change "C." to -- C --.

Column 9,
Line 10, change "moisurizing" to -- moisturizing --.
Line 12, change "04-0.08%" to -- 0.4-0.08% --.
Line 20, delete "-" after "smaller".

Column 10,
Line 1, change "applying" to -- application of --.
Line 23, change "or" to -- of --.

Signed and Sealed this

Eleventh Day of November, 2003

JAMES E. ROGAN
*Director of the United States Patent and Trademark Office*